(12) United States Patent
Zeitouny et al.

(10) Patent No.: US 10,722,726 B2
(45) Date of Patent: Jul. 28, 2020

(54) SKIN TREATMENT SYSTEM

(71) Applicant: KONINKLIJKE PHILIPS N.V., Eindhoven (NL)

(72) Inventors: Mounir Zeitouny, Eindhoven (NL); Calina Ciuhu, Eindhoven (NL); Nathan Alan Gabriele, Eindhoven (NL); Karl Catharina Van Bree, Eindhoven (NL); Leo Jan Velthoven, Eindhoven (NL)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 363 days.

(21) Appl. No.: 15/524,673

(22) PCT Filed: Nov. 3, 2015

(86) PCT No.: PCT/EP2015/075571
§ 371 (c)(1),
(2) Date: May 5, 2017

(87) PCT Pub. No.: WO2016/071325
PCT Pub. Date: May 12, 2016

(65) Prior Publication Data
US 2018/0296853 A1 Oct. 18, 2018

(30) Foreign Application Priority Data
Nov. 6, 2014 (EP) ...................... 14192163

(51) Int. Cl.
*A61B 18/18* (2006.01)
*A61N 5/06* (2006.01)
(Continued)

(52) U.S. Cl.
CPC .......... *A61N 5/0617* (2013.01); *A61B 5/0077* (2013.01); *A61B 5/441* (2013.01);
(Continued)

(58) Field of Classification Search
CPC combination set(s) only.
See application file for complete search history.

(56) References Cited

U.S. PATENT DOCUMENTS 5,394,875 A * 3/1995 Lewis .................. A61B 8/0833
128/916
5,792,147 A * 8/1998 Evans ...................... G06F 19/00
606/130

(Continued)

FOREIGN PATENT DOCUMENTS

DE 102005020723 A1 8/2006
KR 20090059667 A 6/2009
(Continued)

OTHER PUBLICATIONS

Lucas, B.D., Kanade, T., et al.: An iterative image registration technique with an application to stereo vision, IJCAI, vol. 81, pp. 674{679 (1981).
(Continued)

*Primary Examiner* — Michael W Kahelin
*Assistant Examiner* — Shirley X Jian

(57) ABSTRACT

A skin treatment system including a treatment device to treat a treatment region of a body. The skin treatment system includes a camera to capture at least one image of skin, the image having an imaging region, and to provide captured image data representing the captured image. The imaging region has a predefined spatial relationship with the treatment region. The skin treatment system further includes a storage facility for storing reference image data indicative of a reference image of the skin. The skin treatment system further includes an orientation estimation facility to determine which part of the reference image corresponds to the at least one captured image, using the captured image data and the reference image data, and to derive from a predetermined orientation of said corresponding part with respect (Continued)

to the reference image, an orientation indication indicative of an orientation of the treatment device with respect to the body.

20 Claims, 10 Drawing Sheets

(51) Int. Cl.
| | |
|---|---|
| *A61B 5/00* | (2006.01) |
| *A61B 18/20* | (2006.01) |
| *A61B 34/20* | (2016.01) |
| *A61B 18/00* | (2006.01) |
| *A61B 34/10* | (2016.01) |
| *A61B 34/00* | (2016.01) |

(52) U.S. Cl.
CPC ............ *A61B 18/203* (2013.01); *A61B 34/20* (2016.02); *A61B 2018/00452* (2013.01); *A61B 2018/00642* (2013.01); *A61B 2018/00904* (2013.01); *A61B 2034/107* (2016.02); *A61B 2034/2065* (2016.02); *A61B 2034/2074* (2016.02); *A61B 2034/254* (2016.02); *A61N 5/0616* (2013.01)

(56) References Cited

U.S. PATENT DOCUMENTS

| | | | | |
|---|---|---|---|---|
| 6,143,003 | A * | 11/2000 | Cosman | A61B 6/0421 |
| | | | | 128/846 |
| 6,269,143 | B1 * | 7/2001 | Tachibana | A61N 5/1049 |
| | | | | 378/20 |
| 6,405,072 | B1 * | 6/2002 | Cosman | A61B 6/5247 |
| | | | | 600/426 |
| 6,527,443 | B1 * | 3/2003 | Vilsmeier | A61B 6/12 |
| | | | | 378/205 |
| 6,662,036 | B2 * | 12/2003 | Cosman | A61B 6/5247 |
| | | | | 600/411 |
| 6,706,035 | B2 * | 3/2004 | Cense | A61B 18/20 |
| | | | | 606/12 |
| 7,108,690 | B1 * | 9/2006 | Lefki | A61B 18/203 |
| | | | | 606/10 |
| 7,379,531 | B2 * | 5/2008 | Esham | A61N 5/1049 |
| | | | | 378/210 |
| 8,251,908 | B2 * | 8/2012 | Vortman | A61B 5/416 |
| | | | | 600/407 |
| 8,784,407 | B2 * | 7/2014 | Spikker | A61B 18/203 |
| | | | | 606/9 |
| 8,934,605 | B2 * | 1/2015 | Maurer, Jr. | A61N 5/10 |
| | | | | 378/65 |
| 9,405,971 | B2 * | 8/2016 | Qureshi | G06K 9/78 |
| 9,795,443 | B2 * | 10/2017 | Van Hal | A61B 18/203 |
| 10,010,704 | B2 * | 7/2018 | Hyde | A61M 35/00 |
| 2002/0065461 | A1 * | 5/2002 | Cosman | A61B 6/5247 |
| | | | | 600/426 |
| 2002/0188194 | A1 * | 12/2002 | Cosman | A61B 6/5247 |
| | | | | 600/426 |
| 2003/0023235 | A1 * | 1/2003 | Cense | A61B 18/20 |
| | | | | 606/9 |
| 2004/0122311 | A1 * | 6/2004 | Cosman | A61B 6/5247 |
| | | | | 600/427 |
| 2004/0153128 | A1 * | 8/2004 | Suresh | G06F 19/3481 |
| | | | | 607/14 |
| 2006/0210132 | A1 * | 9/2006 | Christiansen, II | A61B 5/0059 |
| | | | | 382/128 |
| 2006/0280287 | A1 * | 12/2006 | Esham | A61N 5/1049 |
| | | | | 378/65 |
| 2008/0058782 | A1 | 3/2008 | Frangineas | |
| 2008/0154257 | A1 | 6/2008 | Sharareh | |
| 2008/0228178 | A1 * | 9/2008 | Van Hal | A61B 18/203 |
| | | | | 606/9 |
| 2008/0269596 | A1 * | 10/2008 | Revie | G06Q 10/087 |
| | | | | 600/424 |
| 2009/0088623 | A1 * | 4/2009 | Vortman | A61B 5/416 |
| | | | | 600/411 |
| 2010/0067660 | A1 * | 3/2010 | Maurer, Jr. | A61B 6/00 |
| | | | | 378/95 |
| 2010/0114080 | A1 * | 5/2010 | Theriault | A61B 18/20 |
| | | | | 606/9 |
| 2011/0022039 | A1 * | 1/2011 | Spikker | A61B 18/203 |
| | | | | 606/9 |
| 2011/0130748 | A1 | 6/2011 | Kellogg | |
| 2011/0206275 | A1 | 8/2011 | Takahashi | |
| 2011/0211665 | A1 * | 9/2011 | Maurer, Jr. | A61N 5/10 |
| | | | | 378/9 |
| 2011/0213253 | A1 | 9/2011 | Kruglick | |
| 2012/0069897 | A1 * | 3/2012 | Anselmo | H04N 19/124 |
| | | | | 375/240.03 |
| 2012/0078088 | A1 * | 3/2012 | Whitestone | A61B 5/0077 |
| | | | | 600/425 |
| 2013/0021460 | A1 | 1/2013 | Burducci | |
| 2013/0085735 | A1 * | 4/2013 | Vilsmeier | G06F 19/3481 |
| | | | | 703/11 |
| 2013/0197357 | A1 | 8/2013 | Green | |
| 2013/0217947 | A1 | 8/2013 | Fishman | |
| 2013/0225969 | A1 * | 8/2013 | Bao | A61B 5/444 |
| | | | | 600/407 |
| 2013/0237973 | A1 * | 9/2013 | Kim | A61B 18/203 |
| | | | | 606/9 |
| 2014/0146190 | A1 | 5/2014 | Mohammadi | |
| 2014/0278229 | A1 | 9/2014 | Hong | |
| 2014/0355834 | A1 * | 12/2014 | Qureshi | G06K 9/78 |
| | | | | 382/103 |
| 2015/0057622 | A1 * | 2/2015 | Hyde | A61M 35/00 |
| | | | | 604/290 |
| 2015/0057623 | A1 * | 2/2015 | Hyde | A61B 5/441 |
| | | | | 604/290 |
| 2015/0254836 | A1 * | 9/2015 | Sako | A61B 1/00009 |
| | | | | 382/128 |
| 2016/0275681 | A1 * | 9/2016 | D'Alessandro | G06T 3/4038 |
| 2016/0324586 | A1 * | 11/2016 | Zingaretti | A61B 17/32053 |

FOREIGN PATENT DOCUMENTS

| | | | | |
|---|---|---|---|---|
| KR | 20110054413 A | | 5/2011 | |
| WO | WO-2007072356 A2 * | | 6/2007 | ........... A61B 5/0064 |
| WO | 2008151343 A1 | | 12/2008 | |
| WO | 2011004285 A1 | | 1/2011 | |
| WO | 2013180420 A1 | | 12/2013 | |
| WO | 2014045558 A1 | | 3/2014 | |
| WO | 2014057481 A2 | | 4/2014 | |

OTHER PUBLICATIONS

Lowe, D.G.: Distinctive image features from scale-invariant key points. International journal of computer vision 60(2), 91{110 (2004).

Rosten, E., Drummond, T.: Machine learning for high-speed corner detection, Computer Vision {ECCV 2006, pp. 430 {443. Springer, (2006).

Rublee, E., Rabaud, V., Konolige, K., Bradski, G.: Orb: an efficient alternative to sift or surf, Computer Vision (ICCV), 2011 IEEE International Conference on, pp. 2564{2571 (2011). IEEE.

\* cited by examiner

SKIN TREATMENT SYSTEM

This application is the U.S. National Phase application under 35 U.S.C. § 371 of International Application No. PCT/EP2015/075571, filed on Nov. 3, 2015, which claims the benefit of International Application No. 14192163.5 filed on Nov. 6, 2014. These applications are hereby incorporated by reference herein.

FIELD OF THE INVENTION

The present invention relates to a skin treatment system comprising a treatment device to treat a mammal body.

The present invention further relates to a method of determining an orientation of a skin treatment device with respect to a mammal body.

The present invention further relates to a skin analysis system for analysis of skin of a mammal body.

The present invention further relates to a method of analyzing skin of a mammal body.

BACKGROUND OF THE INVENTION

Personal treatment devices are known that are equipped with a camera and that use captured camera images to control operation of the device. One example thereof is an interactive hair grooming apparatus as disclosed in US 20130021460. In operation, the known apparatus captures images of the targeted area, uses a translucent superimposed design overlay to determine whether the grooming style is correct, and, if this is not the case, automatically adjusts a grooming trimmer. This way of control is suitable for grooming, as it becomes visible whether or not an observed grooming style complies with a predetermined design style. In this way, it can easily be prevented that an area is treated multiple times, as the known control procedure would determine from the extent of compliance of the captured images with the design overlay whether or not an area had already been treated.

Contrary to this known treatment, many other skin treatments, such as photoepilation, do not result in a directly observable change in appearance of the skin of the body. A user of a device providing such a treatment may notice later that some areas were not treated. Users therefore may tend to overtreat the skin in order to avoid this. This is undesirable, as it implies that the user spends more time than usual to carry out the treatment. For battery-driven devices it implies that a smaller number of treatments can be performed until the battery needs to be recharged or replaced. In certain cases, an overtreatment may also result in skin irritation or even skin damage. A control procedure as used in the known apparatus would not be able to prevent this, as the camera images do not provide information indicating to what extent treatment was completed for the area in the field of view of the camera.

SUMMARY OF THE INVENTION

It is a first object of the present invention to provide a skin treatment system comprising a treatment device to treat a mammal body, which facilitates a user in properly dosing the treatment.

It is a second object of the present invention to provide a method of determining an orientation of a skin treatment device with respect to a mammal body, which facilitates a user in properly dosing the treatment.

It is a third object of the present invention to provide a skin analysis system that is suitable to provide reference data to be used by the aforementioned skin treatment system and/or by the aforementioned orientation determining method.

It is a fourth object of the present invention to provide a method of analyzing skin of a mammal body, that is suitable to provide reference data to be used by the aforementioned skin treatment system and/or by the aforementioned orientation determining method.

According to a first aspect of the invention, a skin treatment system is provided.

According to a second aspect of the invention, a method of determining an orientation of a skin treatment device with respect to a mammal body is provided.

According to a third aspect of the invention, a skin analysis system is provided.

According to a fourth aspect of the invention, a method of analyzing skin is provided.

The skin treatment system according to the first aspect and the method of determining an orientation of a skin treatment device according to the second aspect are based on the recognition that it is possible to use captured images to directly determine the extent to which a treatment complies with a predetermined target, even if the effects of the treatment are not visible in these captured images. In the skin treatment system according to the first aspect and the method of determining an orientation of a skin treatment device according to the second aspect, this is rendered possible in that the captured images are used to determine an orientation of the treatment device with respect to the body. To that end the reference image is used as a map of the skin of the body or a part thereof, and the captured image is compared with the reference image to determine the orientation. By comparing the captured image with the reference image, the orientation estimation facility determines which part of the reference image corresponds to the captured image. Based on the predetermined orientation of said corresponding part of the reference image with respect to the total reference image, the orientation of the captured image with respect to the reference image and with respect to the skin of the mammal body can be determined. Subsequently, based on the predefined spatial relationship between the image region and the treatment region, the orientation of the treatment region or treatment device relative to the mammal body can be determined. The captured image data and reference image data to be compared may comprise image data pertaining to features visible on the skin, such as hairs, surface features of the skin, such as colored spots and skin relief and features visible in the skin, such as blood vessels. Using the orientation, it can be determined to what extent a part of the body corresponding thereto was treated. It is noted that the imaging region of the image captured at a point in time does not need to coincide with the treatment region wherein treatment is being applied at that point in time. It suffices that the imaging region and the treatment region have a predefined, i.e. a known spatial relationship, which is for example determined by mutually predefined, for example mutually fixed positions of the treatment device and the camera in the skin treatment system. It may be advantageous when the imaging region and the treatment region hardly overlap or even do not overlap at all, as the treatment region may be more or less obscured by the treatment device. In the absence of overlap, environmental light may reach the imaging region, so that artificial illumination of the imaging region is superfluous.

The treatment of the body may involve a treatment aiming an effect below the skin surface. For example, painful muscles may be treated by application of infrared (IR) radiation or by vibration. Alternatively, the treatment may aim an effect in the skin, e.g. a treatment of psoriasis by application of UV radiation. Still alternatively, the treatment may be directed to a surface of the skin, e.g. by applying a painting or by changing hair length. Also various treatments may be combined, such as a treatment by infrared (IR) radiation and a massage of muscles by applying vibration.

At each point in time during the treatment, the body is acted upon in a treatment region according to a point spread function, which specifies the intensity with which the body is physically acted upon within the treatment region. The intensity with which the treatment affects the body in the treatment region may be homogeneous. Alternatively, the intensity may be non-homogeneous, for example, it may decrease from a maximum value in a central position within the treatment region to zero at the border of the treatment region. A laser beam, for example as used for phototherapy, typically has a Gaussian distribution. As an alternative, a grooming device may have a substantially rectangular point spread function, wherein the hair length setting of the grooming device is considered as the intensity. The extent to which a treatment has been completed as a function of position on the skin can be determined by a convolution of the point spread function with the path followed by the treatment device being as indicated by the orientation indication. The orientation indication includes at least information indicative of the position of the device on the skin. In addition the orientation information may also include information indicative of the angular position of the treatment device, i.e. the inclination of the treatment device with respect to the surface of the skin, and the rotation of the treatment device in the plane defined by said surface. The latter is particularly relevant if the point spread function strongly deviates from a rotationally symmetrical shape.

The treatment indication $E(x,y)$ indicates an extent to which a treatment was applied to the mammal body as a function of a position on the mammal body. This may be a binary function, e.g. indicating whether or not treatment took place on that location, e.g. indicating whether or not the hair length was trimmed to the desired length in that position. Alternatively, this may be a multi-valued function, e.g. specifying a total exposure to radiation received at that position, i.e. the integral of the intensity of the received intensity over time. This integration time may be the duration of the current treatment, but it may also take into account previous treatments. Again alternatively, the treatment indication may have a limited set of values, for example a value indicative of undertreatment, proper treatment and overtreatment, respectively. Alternatively, further nuances may be applied to this scale.

In an embodiment, said treatment indication $E(x,y)$ may be provided to the user. To that end, the skin treatment system may further comprise a display (either integrated in the treatment device or as part of a separate device, such as a mobile phone) to provide a visual representation of the treatment indication for example. The treatment indication may be superposed on an image of the (sub-)region of the skin to be treated. In addition, a global image of the mammal body or a model thereof may be shown including an indication thereon of the location of the (sub-)region of the skin to be treated. A comparison facility may be provided to compare said extent as indicated by the treatment indication with a target to be achieved and to provide a compliance indicator representative of the extent of compliance as a function of the position on the skin, wherein the compliance indicator is used to provide a visual representation of said treatment indication ($E(x,y)$). Alternatively, the indication may be visually represented in the form of a color map or a gray value map. In this way the user can monitor progress of the treatment on the display and properly dose the treatment, without missing areas or overtreating areas.

In an embodiment, a controller is provided to control the treatment device and the controller is arranged to control the treatment device in accordance with the treatment indication. Also in this embodiment, a display may be present to provide a visual representation of the treatment indication.

A comparison facility may be provided to compare the extent as indicated by the treatment indication with a target to be achieved. The target to be achieved may have a fixed value for the entire skin region to be treated. Alternatively, the target to be achieved may be position-dependent. For example, the target to be achieved may be a desired hair-cut pattern, specifying a desired hair length as a function of position. A storage unit may be provided to store the desired pattern. The comparison facility which may be integrated in the controller, may provide a compliance indicator representative of the extent of compliance as a function of the position on the skin, wherein the compliance indicator is used to control the treatment device. The controller may for example switch off the treatment device at locations of the skin that were sufficiently treated. Alternatively, the degree to which the treatment device applies its physical effect to the skin may be more gradually controlled in a range between a minimum and a maximum, depending on an extent to which treatment is completed. In certain circumstances the degree to which the treatment device applies its physical effect to the skin may be increased over time. Embodiments may be contemplated for example wherein photon radiation is applied to the skin, and wherein an intensity of said photon radiation is set to a relatively low value during initial treatments, while the intensity is set relatively high during later treatments.

The skin treatment system according to the first aspect may be provided as one unit. That is to say, all its parts may be integrated in a housing provided for the treatment device. In an alternative embodiment, the skin treatment system according to the first aspect is provided as an arrangement of a body treatment module and a processing module which are mutually functionally coupled and, at least within an operational range, independently movable with respect to each other, wherein the body treatment module at least comprises the treatment device and the camera integrated therewith, and wherein the processing module at least comprises the storage facility and the orientation estimation facility. The functionality of the processing module can be provided by suitably programming a general purpose device, such as a notebook, a PDA or a mobile phone, using the storage medium. In this way, the number of components of the treatment device can be modest.

The operational range may be determined by the length of a cable in the case of a wired coupling between the skin treatment module and the processing module. In case these modules are functionally coupled in a wireless manner, the transmission range may determine the operational range. Alternatively, the modules may each be coupled via a general communication network, such as the internet. In the latter case, the processing module may be a remote server, for example.

As indicated above, the treatment may affect the body below the skin surface, in the skin surface or above the skin surface, depending on the desired result. In particular, an embodiment is contemplated wherein the treatment device is a photon radiation device to irradiate the skin with photon radiation to physically affect the mammal body in the treatment region, e.g. for photo-epilation or for treatment of psoriasis.

In particular, a further embodiment is contemplated wherein the treatment device is a hair clipper arranged to clip hairs on the skin in the treatment region to physically affect the mammal body in the treatment region.

In an embodiment, the skin treatment system according to claim 1 further comprises an update unit to receive captured image data and to use said captured image data to update said reference image data.

The actual appearance of the skin may gradually change with time due to ageing, changing weight, changing of skin color due to pigmentation as a result of UV-radiation and the like. This may have the effect that over time it becomes more difficult to determine which part of the reference image corresponds to the captured image. One approach to address this issue would be to scan the body from time to time to prepare fresh reference image data. In an embodiment, the system includes an update unit that uses said captured image data to update the reference image data. The update unit may observe gradual changes of features in said captured image data and adapt the reference image data in accordance with these observations. In this way, image features in a captured image will always closely resemble the features in the corresponding portion of the reference image, enabling localization of a matching reference image portion. If, however, the reference image data is not updated, a situation may occur over time wherein the discrepancy between the features as observed in the captured image no longer matches a corresponding feature in the reference image. An example may be a feature representative of a distance between two pores in the skin. As a result of a gain in weight, such a distance will increase. The reference image data can be updated to take into account this gradual change. A model of the mammal body may be used to improve the quality of the update. For example, an increasing body weight will have a global effect on the appearance of the skin. By using a model that predicts this global effect, and using the observations obtained over a large area of the skin, it can be determined more accurately whether an observed change in a feature is indeed due to a weight change or to another cause, e.g. noise. Alternatively or in addition, an update unit may update the stored reference image on the basis of a model specifying an expected development over time of features therein.

A reference image as used by the skin treatment system according to the first aspect and the orientation determining method according to the second aspect can be obtained by a skin analysis system according to the third aspect as defined below. A skin analysis system according to the third aspect for analysis of skin of a mammal body comprises:

a skin imaging camera which is configured and arranged such that, in an operational state of the skin analysis system, the skin imaging camera captures a plurality of images of said skin, and provides respective image data representative of said plurality of images, an orientation determining device which is configured and arranged such that, in the operational state of the skin analysis system, the orientation determining device provides respective orientation information data representative of an orientation of the skin imaging camera, an image mapping unit which is configured and arranged such that, in the operational state of the skin analysis system, the image mapping unit maps said respective image data in dependence on the orientation of the skin imaging camera at which the image data was respectively obtained as indicated by said respective orientation information data, and provides respective mapped image data representing the result of this mapping, and an image merging unit which is configured and arranged such that, in the operational state of the skin analysis system, the image merging unit prepares a single merged image from the respective mapped image data, and provides merged image data, representing the single merged image, for use as the reference image.

Analogously, a method of analyzing skin of a mammal body according to the fourth aspect is provided, with which the reference image can be generated. The method according to the fourth aspect comprises the steps of:

capturing a plurality of images of said skin by means of a skin imaging camera and providing respective image data representative of said plurality of images, providing respective orientation information data representative of an orientation of the skin imaging camera at which said plurality of images are respectively captured, mapping said plurality of images in dependence on the orientation of the skin imaging camera at which the respective image data was obtained as indicated by said orientation information data, and providing respective mapped image data representing the result of this mapping, preparing a single merged image from the respective mapped image data, and providing merged image data, representing the single merged image, for use as the reference image.

The merged image (also denoted as stitched image) for use as the reference image may be a two-dimensional image that includes the raw image data, such as the color as defined by an RGB value or a YUV value. Additionally, the merged image for use as the reference image may specify a distribution of specific features over the skin. Such features may be hair color, density, length and thickness, but may alternatively be features specific for the skin itself, e.g. pigment spots, and a profile of the skin. In addition, the observed orientation of the normal of the skin may be added to the map. Accordingly, the reference image may be provided as a vector including one or more values indicative of a color, observed features, and the observed surface normal. It is noted that the observed surface normal depends on the posture of the body during analysis, which posture may be different during treatment. However, provided that the treated part of the body does not move during the treatment, the change of the observed surface normal should be consistent with the displacement of the treatment device over the skin, and can be used as a clue in locating the current orientation of the treatment device of the skin. If the treated part of the body is not stably positioned, input from an external camera may be used to estimate the contribution of the movements of the treated body part to the observed changes in the surface normal.

In an embodiment of the skin analysis system, the orientation-determining device comprises a gyroscope. A gyroscope enables an accurate determination of the absolute orientation at which the images are captured. Alternatively, or additionally, the orientation-determining device may comprise a further camera, having a field of view including at least a part of the skin-imaging camera and at least a part of the mammal body. This alternative or additional measure is particularly useful if the body part to be scanned is not stably positioned. In a further alternative embodiment, an orientation of the images to be merged may be determined from the orientation of features in mutually overlapping parts of the image to be merged and the merged image obtained so far from earlier captured images of the skin.

As indicated above, the surface normal may be an additional feature in the merged image. The observed surface normal of the skin during scanning may deviate from the actual surface normal of the skin. These deviations may be due to deformations caused by pressure exerted on the skin by the scanning device or the operator not holding the scanning device perpendicularly to the skin surface. In an embodiment, a 3D profile as obtained from the merged image data is compared with a generic 3D body profile and a corrected 3D profile is provided on the basis of this comparison. The skin analysis system according to the third aspect may comprise a correction facility for this purpose. The generic 3D body profile may provide a general expression for the shape of the skin of the body part to be scanned. By fitting the observed data to this general expression, a more accurate estimation of the surface normal is possible.

In an embodiment, the skin treatment system according to the first aspect of the invention further includes a skin analysis system according to the third aspect of the invention, wherein the skin analysis system is configured and arranged such that, in the operational state of the skin analysis system, the image merging unit of the skin analysis system prepares the reference image from the respective mapped image data mapped by the image mapping unit of the skin analysis system. In this way, a single scanning and treatment device is provided. The operator that performs the scanning procedure to obtain the merged image as the reference image may hand over the single scanning and treatment device to the customer, who may subsequently perform the treatment with that device. This would be advantageous in the sense that various components may serve a dual purpose. For example, a single camera may be used to capture the images for obtaining the merged image, and to capture images during treatment to determine an instantaneous orientation of the device. Also various data processing facilities may be combined in the single device, as well as storage facilities.

Nevertheless, it may be advantageous to provide the skin treatment system according to the first aspect and the skin analysis system according to the third aspect as separate devices. This would make it possible to highly optimize the skin analysis system according to the third aspect, as one species of this system can be used for preparation of reference images for a plurality of users of the treatment system. The cost of the treatment system can be modest, particularly when parts (i.e. the data processing facilities) of the treatment system are implemented by already available devices, such as a mobile phone or a notebook. Accordingly, an embodiment of the skin treatment system according to the first aspect includes a data exchange facility to enable transfer of said merged image data to an external device. The data exchange facility may be provided for example in the form of a detachable memory that can be decoupled from the skin treatment system according to the first aspect after the merged image to be used as the reference image is prepared, and which detachable memory can be coupled to the skin treatment system according to the first aspect before using it for treatment. Alternatively, transfer of the merged image from the skin analysis system according to the third aspect to the skin treatment system according to the first aspect may take place by a wireless or wired connection. A wireless connection may be established in a direct manner, e.g. via a Bluetooth connection, or indirectly, e.g. via the internet.

BRIEF DESCRIPTION OF THE DRAWINGS

These and other aspects are described in more detail with reference to the drawing. Therein.

DETAILED DESCRIPTION OF EMBODIMENTS

Like reference symbols in the various drawings indicate like elements unless otherwise indicated.

Figure 1:
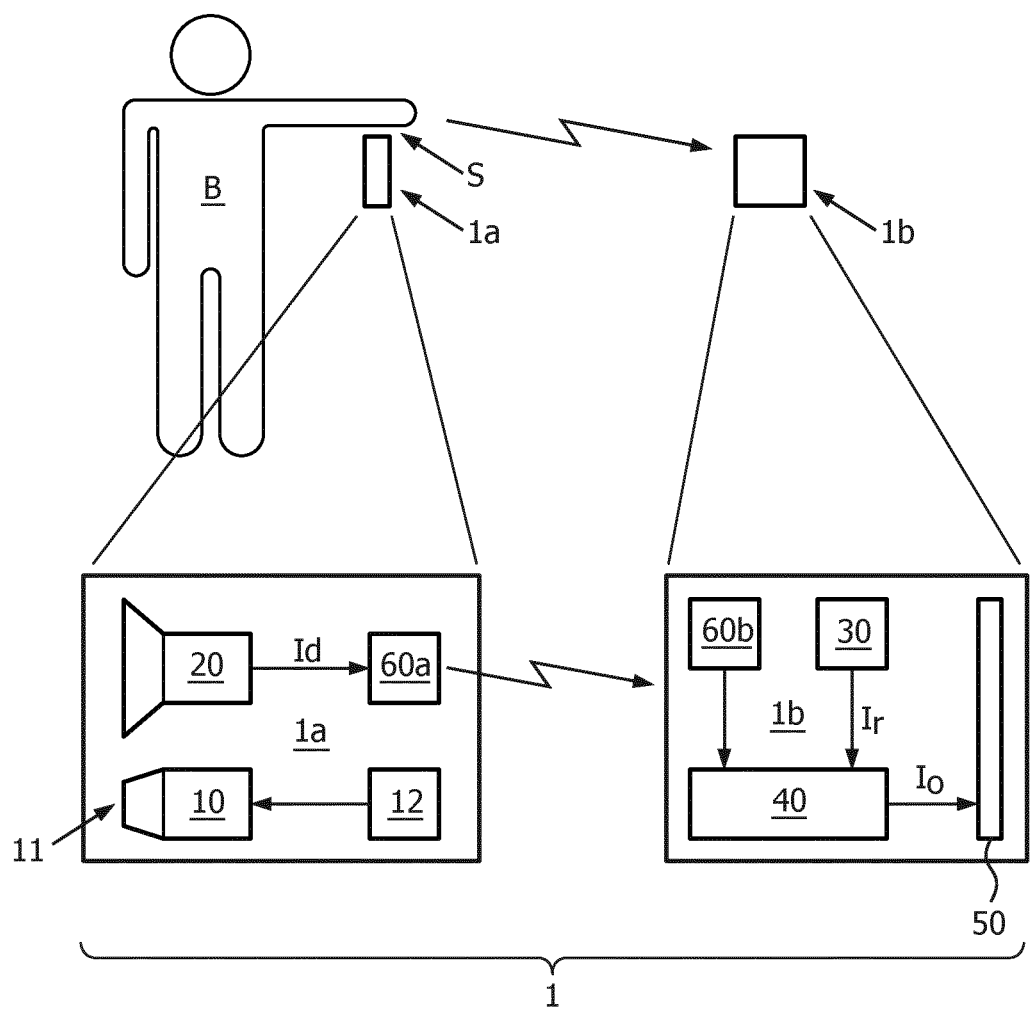
FIG. 1 illustrates an embodiment of a skin treatment system according to the first aspect of the invention.
Figure 2A:
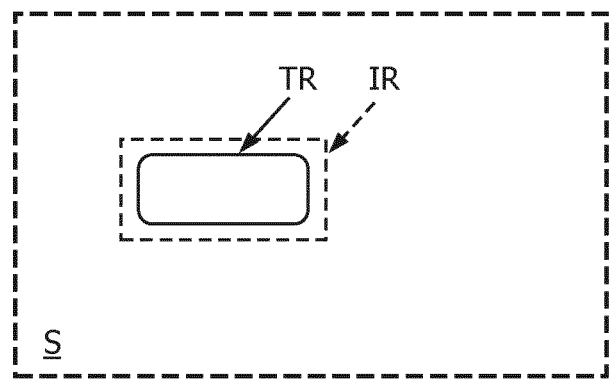
FIGS. 2A, 2B, 2C illustrate examples of a spatial relationship between a treatment region and an imaging region.
Figure 2B:
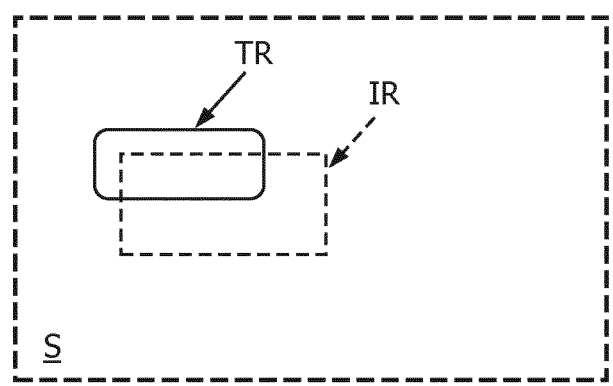
Figure 2C:
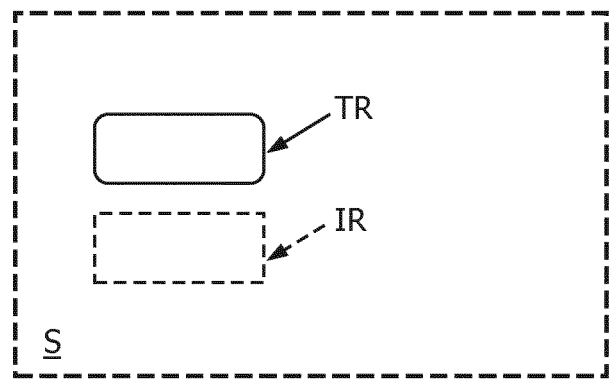

FIG. 1 schematically shows a skin treatment system 1 comprising a treatment device 10 to treat a treatment region TR, See FIGS. 2A-C, of a mammal body B by physically acting upon the body in the treatment region. In the embodiment shown, the system 1 is provided as a treatment unit 1*a* and a processing unit 1*b*. As will be exemplified later with reference to FIGS. 6, 8 and 9, the system may alternatively be provided as a single unit. The treatment device 10 may for example be one of: a massage treatment device, a radiation treatment device, for example by applying infrared or ultraviolet radiation, or a grooming device.

In addition to the treatment device 10, accommodated in treatment unit 1*a*, the skin treatment system 1 further comprises a camera 20 to capture at least one image of skin S of the mammal body, said image having an imaging region IR in front 11 of the unit 1*a*, See FIGS. 2A-C, and to provide captured image data Id. This captured image data is representative of the at least one captured image. The imaging region IR has a predefined, i.e. a known spatial relationship with respect to the treatment region TR, but it is not necessary that the imaging region IR and the treatment region TR coincide, as indicated in FIG. 2A. Alternatively, these regions may partly overlap (FIG. 2B) or even be disjoint (FIG. 2C). It is even favorable if the regions are disjoint, as in the latter case it is not a problem if the treatment device occludes the treatment region TR. The predefined spatial relationship between the imaging region IR and the treatment region TR is for example determined by the mutually predefined, for example mutually fixed positions of the treatment device 10 and the camera 20 in the treatment unit 1a.

The skin treatment system 1 includes a control element 12 for controlling the treatment device 10. The control element 12 may be a simple switch, a magnitude controlling element, or a timer, but as will be described in more detail later, it may also include more advanced capabilities. In this case, the control element 12 is accommodated in the treatment unit 1a, but alternatively, it may be accommodated in the processing unit 1b.

The skin treatment system 1 also comprises a storage facility 30, here also accommodated in processing unit 1b. The storage facility 30 stores reference image data Ir, indicative of a reference image of the skin of the mammal body B. The reference image data may comprise one or more of: raw image data, such as RGB data, HUV data, or gray value data, feature descriptor data, that specify the presence of specific features on the skin, of the skin or in the skin as a function of position, and/or surface normal data, indicative of a surface normal of the skin as a function of position. The term "indicative" is used here, as it is generally not known what the absolute orientation of the surface normal of the skin is, unless the body is stabilized in a reference position. However, the surface normal data may specify how the surface normal of the skin changes relative to the skin position for a particular body part.

The skin treatment system 1 also includes an orientation estimation facility 40 to determine which part of said reference image corresponds to the at least one captured image, using the captured image data Id and said reference image data Ir. Using this information, the orientation estimation facility provides an orientation indication Io indicative of an orientation of the treatment device with respect to the body B.

In the embodiment shown, the orientation estimation facility 40 is a general purpose processor, accommodated in the processing unit 1b, that is suitably programmed to identify which region in the reference image matches the region as captured from the imaging region, and to return the location of this region on the skin of the body B, which can for example be derived based on a predefined relationship between the identified region of the reference image and the position on the skin of the bpdy B. From this location, the location of the treatment region TR can be determined, as it has a predefined, for example fixed spatial relationship with the imaging region IR. In the embodiment shown, the captured image data is transmitted via transmitter 60a of treatment device 1a to receiver 60b of processing unit 1b, and provided to the general purpose processor 40. Alternatively, this data transfer may take place via a wired connection.

The location of the matching region in the reference image may be determined in various ways. According to one approach, a reference image comprising raw image data is used, and compared with raw image data available in the captured image data. The location in this case may be determined, for example, as the location having a local minimum of the normalized correlation function. An example of this approach is described in more detail in Lucas, B. D., Kanade, T., et al.: An iterative image registration technique with an application to stereo vision, IJCAI, vol. 81, pp. 674{679 (1981). Similarly, the angle at which the captured image was obtained may be determined in this way. In case the imaging region and the treatment region coincide and the effect of the treatment is a rotationally symmetrical function it is not necessary to know this angle.

According to another approach, instead of comparing raw image data, a comparison is made between predetermined features detected in the captured image and present in the reference image. Various algorithms are available for detection of such features. Typically, these algorithms select image areas where large intensity gradients are found. Examples of these kinds of algorithms are known as SIFT, FAST and ORB. A more detailed description thereof is available, respectively, in:

Lowe, D. G.: Distinctive image features from scale-invariant key points. International journal of computer vision 60(2), 91{110 (2004).

Rosten, E., Drummond, T.: Machine learning for high-speed corner detection, Computer Vision {ECCV 2006, pp. 430{443. Springer, (2006), and Rublee, E., Rabaud, V., Konolige, K., Bradski, G.: Orb: an efficient alternative to sift or surf, Computer Vision (ICCV), 2011 IEEE International Conference On, pp. 2564{2571 (2011). IEEE.

As a result of this detection, a feature vector F is obtained as a function of image position (x,y). Subsequently, the feature vector Fd(x,y) for the captured image and the feature vector Fr(x,y) for the reference image are compared to determine the location where the best match is found and optionally the angle for which the best match is found. A method for this purpose is also described by Rublee et al. referred to above.

The computation of the feature vector Fd(x,y) for the captured image may be performed in the treatment unit 1a, but is preferably performed in the processing unit 1b, so as to optimally use available processing facilities in the processing unit 1b. In order to minimize bandwidth requirements for the connection between the treatment unit 1a and the processing unit 1b, it may be contemplated to apply data compression to the captured image data Id before transmission thereof and to apply decompression upon receipt. Also channel coding and channel encryption technologies may be applied to this connection.

Figure 3:
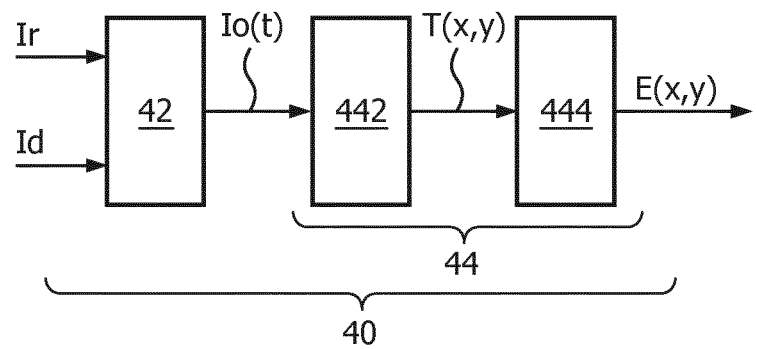
FIG. 3 illustrates a part of an embodiment of a skin treatment system according to the first aspect of the invention.

An embodiment of the data processor of the orientation estimation facility 40 of processing unit 1b is shown in FIG. 3. The orientation estimation facility 40 is shown here as a first module 42 of the data processor. In addition, the orientation estimation facility 40 includes an analysis facility 44 that uses the orientation indication Io to provide a treatment indication E(x,y). The treatment indication E(x,y) is indicative of an extent to which a treatment was applied to the mammal body B as a function of the position thereon. The analysis facility includes a first stage 442, that computes a tracking indication T(x,y), which is indicative of the trail of treatment locations during the treatment, and a second stage 444 that convolves the tracking indication T(x,y) with the point spread function PSF(x,y) specifying the effect of the treatment device in the neighborhood of the treatment location. These steps are schematically illustrated in FIGS. 4A, 4B.

Figure 4A:
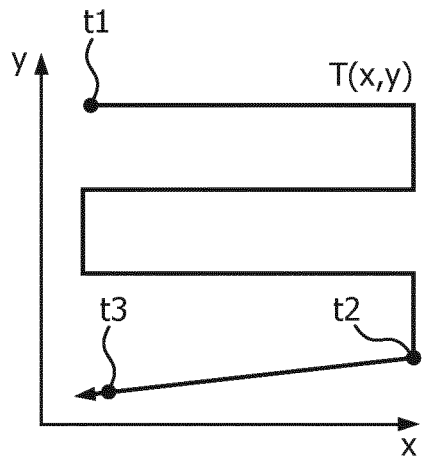
FIGS. 4A, 4B illustrate example processed image data.
Figure 4B:
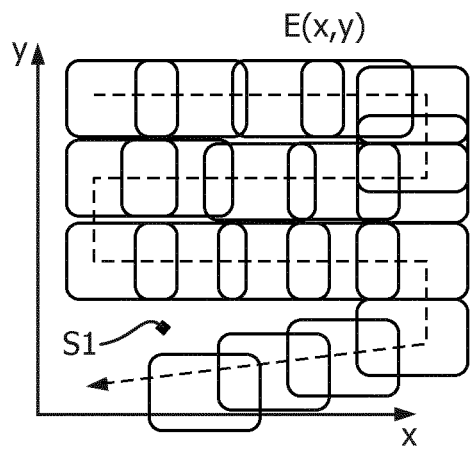

FIG. 4A shows an example of a trail followed, as indicated by a tracking indication T(x,y). In this case, the consumer moved the treatment unit 1a over the skin S according to a regular meandering pattern during a time interval t1-t2, but subsequently deviated from this regular pattern in the time interval t2-t3. The tracking indication T(x,y) may be a binary indication, merely indicating whether or not a location is part of the trail. Alternatively, the tracking indication T(x,y) may specify, for each position x,y, a length of a time interval during which the identified location Io coincided with position x,y.

The second stage 444 may calculate the treatment indication E(x,y) by the following operation:

$$E(x, y) = \iint_{x',y'} PSF(x - x', y - y')T(x', y')dx'dy'$$

if the effect of the treatment is proportional to the intensity with which the body is physically acted upon as indicated by the point spread function PSF and the duration as indicated by the tracking indication T(x,y).

If the effect is a non-linear function f of these terms, the treatment indication E(x,y) may be calculated as:

$$E(x, y) = \iint_{x',y'} f(PSF(x - x', y - y')T(x', y'))dx'dy'$$

In some cases, the effect of the treatment may be expressed by a binary function. For example, when grooming a beard to a specific length, no further change occurs if the grooming device's presence on the treatment area exceeds a predetermined minimum time.

In that case, the treatment indication E(x,y) may be calculated as:

$$E(x, y) = BIN\left(\iint_{x',y'} PSF(x - x', y - y')T(x', y')dx'dy'\right),$$

wherein the point spread function PSF specifies the grooming region as a binary function, which is equal to 1 inside the grooming region and 0 outside the grooming region. Furthermore, the following function applies: BIN(z)=0 if $z<z_T$, and 1 if $z \geq z_T$, wherein $z_T$ is the predetermined minimum time.

By way of example, FIG. 4B illustrates how the treatment indication E(x,y) may be calculated from the tracking indication T(x,y). As mentioned above, with reference to FIG. 4A, in time interval t1-t2, the user moved the treatment unit 1a over the skin according to a regular meandering pattern. The meandering pattern includes horizontal parts (extending in the x direction) and vertical parts during which the user moves to a next horizontal part. During the first time interval t1-t2, the distance between the horizontal parts was maintained at a value corresponding to a dimension of the treatment region TR in the y-direction. Accordingly, it is therewith achieved that the area of the skin in which the treatment unit 1a is moved during the time interval t1-t2 is fully covered, as is schematically illustrated in FIG. 4B for a part of that area. For clarity, it is assumed here that the pointspread function PSF(x,y) is a function which has a constant value inside the treatment region TR, and which is 0 outside the treatment region. Alternatively, when the point spread function PSF decreases towards the edges of the treatment region, the user may perform the meandering movement along horizontal lines that are more closely arranged with respect to each other.

As also noted before, the user may accidentally deviate from the predetermined pattern, as illustrated here for the time interval t2-t3. As can be seen in FIG. 4B, this has the effect that the area traversed by the treatment unit 1a is not completely treated, for example as illustrated by portion S1 in FIG. 4B. This could remain unnoticed for some time if the treatment has a delayed effect. This is for example the case with a photoepilation treatment. The user might try to avoid this by repeating the treatment or by minimizing the vertical displacement of the treatment device when meandering over the skin's surface. This however would cost the user more time than strictly necessary to perform the treatment and could also result in overtreatment, possibly causing skin irritation According to the skin treatment system as disclosed in the present invention, an orientation indication Io is computed from the image captured by the camera integrated in the treatment unit 1a. Using this orientation indication, the effect of the treatment can be computed even if this is not visible during the treatment.

In the embodiment shown in FIG. 1, the skin treatment system 1 further comprises a display 50 to provide a visual representation of said treatment indication E(x,y). In this case, the display is part of the processing unit 1b, for example as a display of a mobile phone. This display 50 allows the user to monitor the progress of the treatment. In this way, the user can immediately notice whether certain regions of the area to be treated were missed or likely to be overtreated. Upon noticing this, the user can correct the treatment trajectory to treat the missed regions and avoid or mitigate overtreatment. This enables the user to efficiently treat a predetermined area.

Treatment indication E(x,y) may be represented on the display in various ways, for example as a binary function, indicating for each position whether or not it is treated, a gray value, for example with a brightness proportional to the treatment indication E(x,y), or a ternary indication, for example using the color blue to indicate undertreatment or no treatment, green to indicate proper treatment and red to indicate overtreatment. The representation of the treatment indication E(x,y) may be superposed on an image of the body or the part thereof to be treated.

Figure 5:
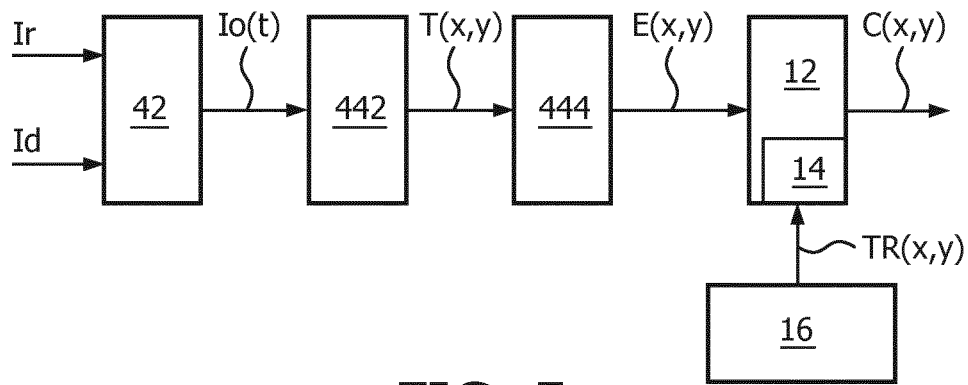
FIG. 5 illustrates parts of an embodiment of a skin treatment system according to the first aspect of the invention.

In an embodiment as shown in FIG. 5, the skin treatment system further comprises a controller 12 to control the treatment device 10 in accordance with said treatment indication E(x,y). This functionality may be provided instead of or in addition to the functionality as provided by the system of FIG. 1.

As shown in FIG. 5, the skin treatment system includes a storage module 16 on which a treatment requirement specification TR(x,y) is stored, which specifies the extent to which a treatment should be applied as a function of the position x,y on the skin. The controller 12 includes a module 14 that compares the treatment indication E(x,y) with the treatment requirement specification TR(x,y) and provides control signals C(x,y) that control the treatment device 10 to optimally match the treatment requirement specification TR(x,y). This may be achieved in various ways. The module 14 may for example simply switch off the treatment device 10 if an area is likely to be overtreated, but it may alternatively moderate the intensity with which the treatment device 10 acts upon the body in the neighborhood of the location x,y. Also, in some embodiments, the controller may adapt the point spread function PSF(x,y) of the treatment device 10. It is noted that the treatment requirement specification TR(x,y) may be time-dependent. The specification TR(x,y) may for example specify a gradual increase in the intensity with which the body is acted upon and/or a change of the duration of the treatment.

In case the skin treatment system 1 includes a controller for automatically controlling the treatment device 10 in accordance with an observed treatment indication E(x,y) and a treatment requirement specification TR(x,y), it is not necessary to display the treatment indication E(x,y) to the user. Nevertheless, it is favorable if these two functionalities are combined. For example, if the treatment device is primarily controlled by the user, the automatic controller 12 may override user control, for example by switching off the treatment device if the user, despite the displayed treatment indication E(x,y), accidently is about to overtreat a region. Alternatively, if the treatment device is mainly controlled by controller 12, the display 50 can provide the user feedback about the progress of the treatment.

Figure 6:
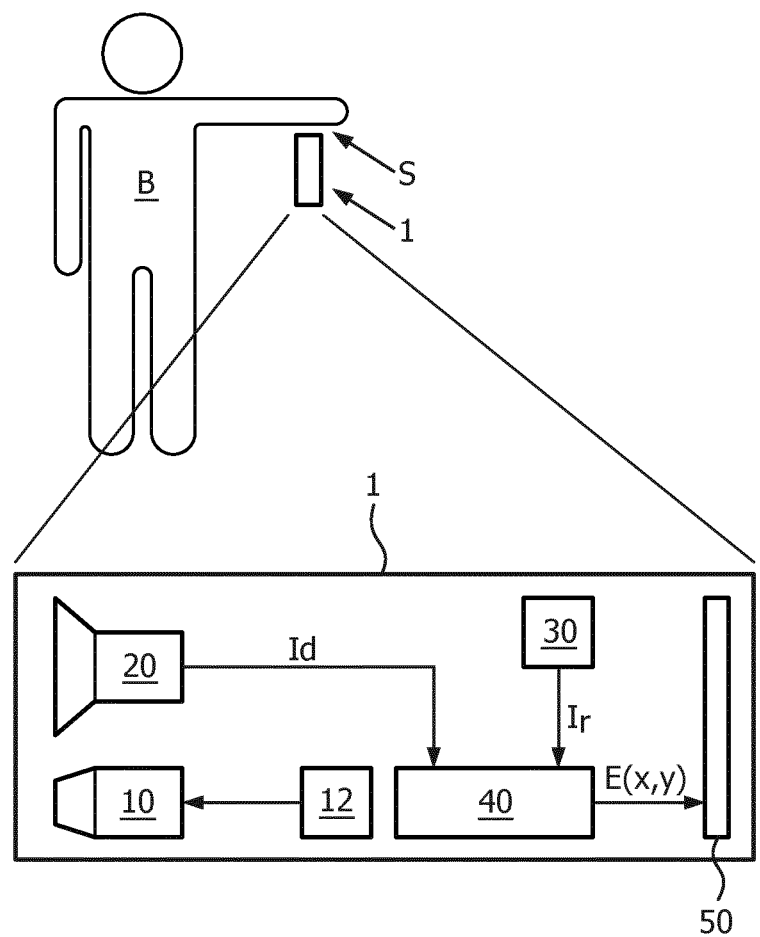
FIG. 6 illustrates an embodiment of a skin treatment system according to the first aspect of the invention.

FIG. 6 shows an example of an embodiment of the skin treatment system 1, which is provided as a single unit. In this case, signal transfer facilities (e.g. 60a, 60b in FIG. 1) for transferring captured image data Id, or processed versions thereof, are superfluous, as the captured image data Id can be directly provided to the orientation estimation facility 40. Otherwise, however, the skin treatment system 1 as shown in FIG. 6 is equivalent to the system 1 as shown in FIG. 1.

Figure 7:
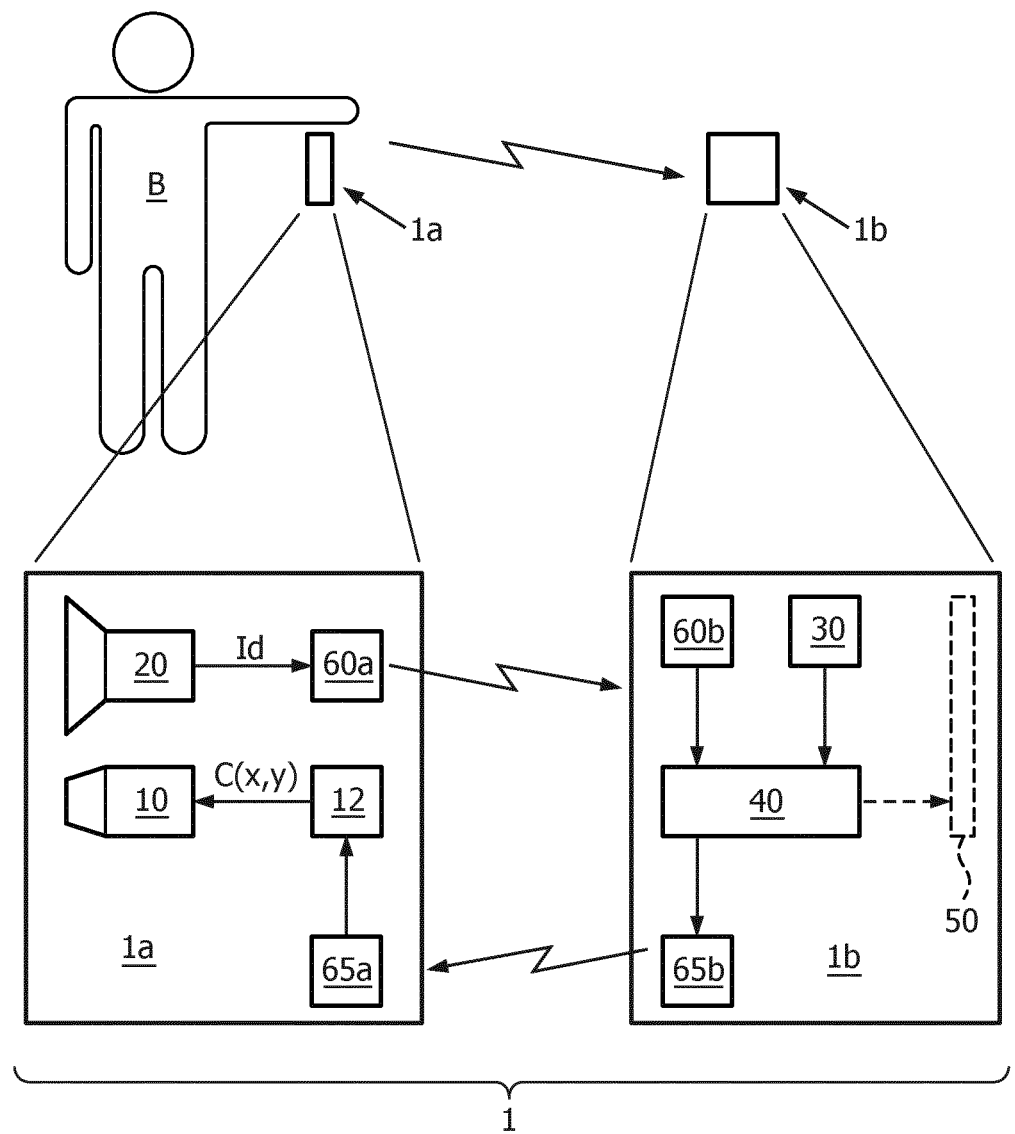
FIG. 7 illustrates an embodiment of a skin treatment system according to the first aspect of the invention.
Figure 13:
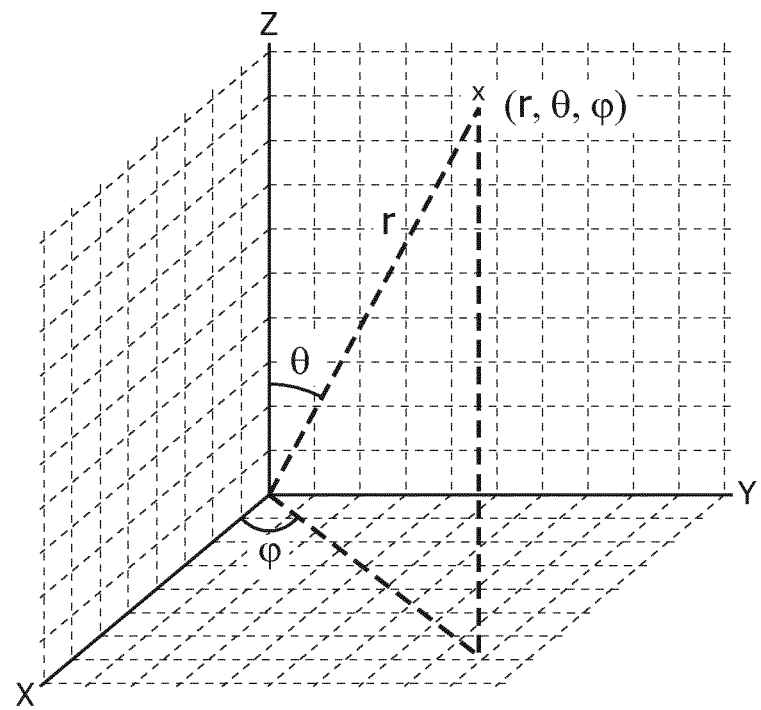

FIG. 7 shows an embodiment of the skin treatment system 1, wherein the controller 12 is capable of controlling the treatment device 10 in accordance with the treatment indication E(x,y). As in the previously described embodiments, the camera 20 provides captured image data Id, which is used to determine an orientation indication. The captured image data Id or a processed version is transmitted by transmitter 60a of treatment unit 1a to receiver 60b of processing unit 1b. And the orientation estimation facility 40 uses this data to estimate the orientation of the treatment device with respect to the body B, in terms of a position on the skin. The orientation may additionally include information about the azimuthal angle θ, and polar angle φ with respect to the surface normal to the skin, as illustrated in FIG. 13. The required data processing operations necessary to determine how the treatment device 10 must be controlled to optimally meet the treatment requirement specifications may be carried out by the processor 40, by the controller 12, or by a combination thereof. Intermediary signals are transmitted, from processor 40, by transmitter 65b of processing unit 1b via receiver 65a of unit 1a to controller 12. Optionally, the processing unit 1b may have a display 50 to enable the user to monitor treatment progress.

Figure 8:
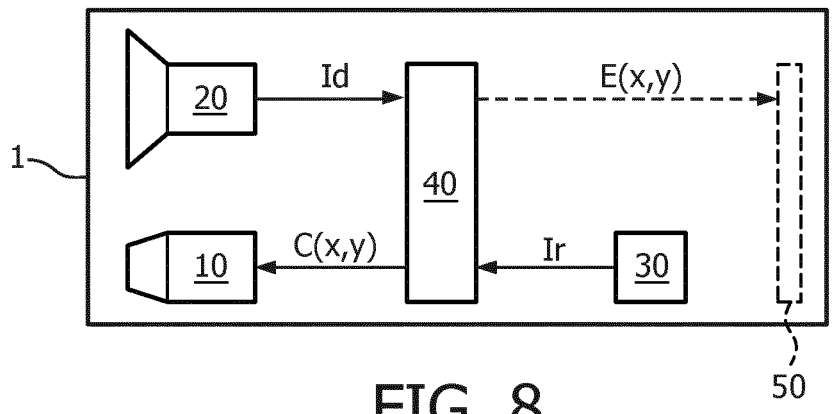
FIG. 8 illustrates an embodiment of a skin treatment system according to the first aspect of the invention.

The system of FIG. 7 may also be implemented in a single unit, as illustrated in FIG. 8.

Figure 9:
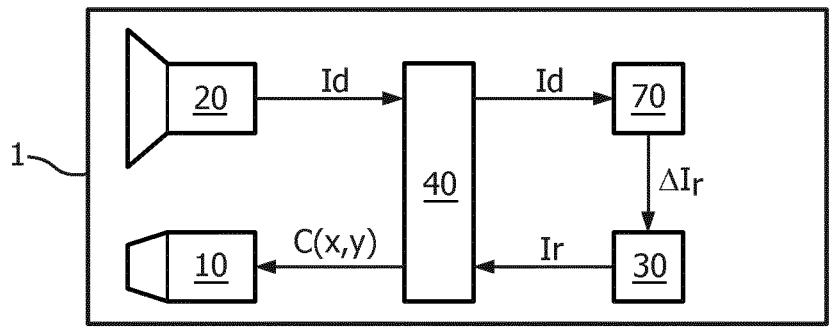
FIG. 9 illustrates an embodiment of a skin treatment system according to the first aspect of the invention.

FIG. 9 shows a further embodiment, wherein the skin treatment system 1 further comprises an update unit 70 to update, as symbolically indicated by signal ΔIr, the reference image data Ir stored in storage facility 30.

To this end, the update unit 70 may observe gradual changes of features in the captured image data Id and adapt the reference image data Ir stored in storage facility 30 in accordance with these observations. Alternatively or in addition, the update unit 70 may update the stored reference image on the basis of a model specifying an expected development over time of features therein.

In this way, image features in a captured image always will closely resemble the features in the corresponding portion of the reference image, enabling localization of a matching reference image portion. If, however, the reference image data is not updated, a situation may occur, at a future point in time, wherein the discrepancy between the features as observed in the captured image no longer matches a corresponding feature in the reference image.

Figure 9A:
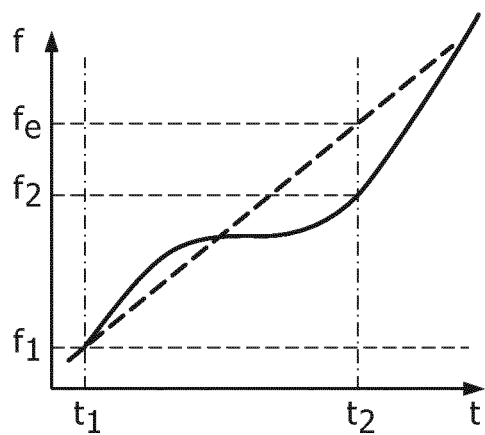
FIGS. 9A, 9B illustrate an operation of the embodiment of FIG. 9.

Two examples illustrating how this may be take place are described with reference to FIGS. 9A and 9B, respectively. In both figures, the solid line illustrates the actual progress of a feature f as a function of time t. By way of example, the feature f in FIG. 9A is a length of a hair, growing from a particular location. In the reference image prepared at time $t_1$, and stored in storage facility 30, the value for this feature is $f_1$. Due to growth, the length of the hair has increased to $f_2$ at point in time $t_2$. If this feature f is used when aiming to locate the captured image in the reference image, the difference $f_2-f_1$ may be too large to be used as evidence to support the match, thereby rendering this feature unsuitable for use by the orientation estimation facility. However, if the current value of the feature f is predicted on the basis of the previous value $f_1$ and the expected growth, as illustrated by the dashed line extending in the direction $(t_1,f_1)$ to $(t_2, f_e)$, a more accurate estimation $f_e$ of the current value of the feature f is obtained, facilitating a proper recognition.

Figure 9B:
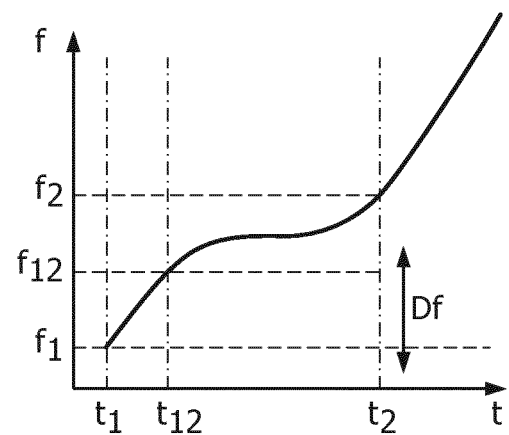

As another example, FIG. 9B shows how the update unit 70 may update the reference image data on the basis of intermediary observations for the feature f. In this example, it is assumed that the value Df is a recognition threshold for a feature f. That is to say, if and only if the absolute value of the difference between the observed value of the feature and the value stored for said feature in the reference image is less than this threshold value, the feature is determined to match. In this example, it is again assumed that the feature f has a value $f_1$ at time $t_1$. Further, it is assumed that the user uses the treatment system 1 at an intermediary point in time $t_{12}$. At this intermediary point in time, the value of the feature f has changed from $f_1$ to $f_{12}$. As $|f_{12}-f_1|<Df$, the feature f in the captured image will be recognized as part of the reference image stored in storage facility 30. It is supposed that the user again uses the treatment system 1 at the point in time $t_2$, and that the value of the feature f has changed to $f_2$. Now $|f_2-f_1|>Df$, so that the feature f in the captured image will not be recognized as part of the reference image stored in storage facility 30. However, in the embodiment wherein the value for the feature f is updated, by unit 70, to the observed value $f_{12}$, the feature f would still be recognized, as $|f_2-f_{12}|<Df$.

It is noted that, in practice, the decision whether the captured image and a part of the reference image match may be based on a comparison of respective observed and stored values for a plurality of features. Furthermore, a weighting may be applied to the result of this comparison, that assigns more weight to more reliable and/or more relevant features than to less reliable and/or less relevant features. Nevertheless, also in this case a more reliable determination of the location of the part of the reference image that matches the captured image can be obtained if the data in the reference image is updated on the basis of intermediate observation and/or on the basis of a model for the development of these features as a function of time.

Figure 10:
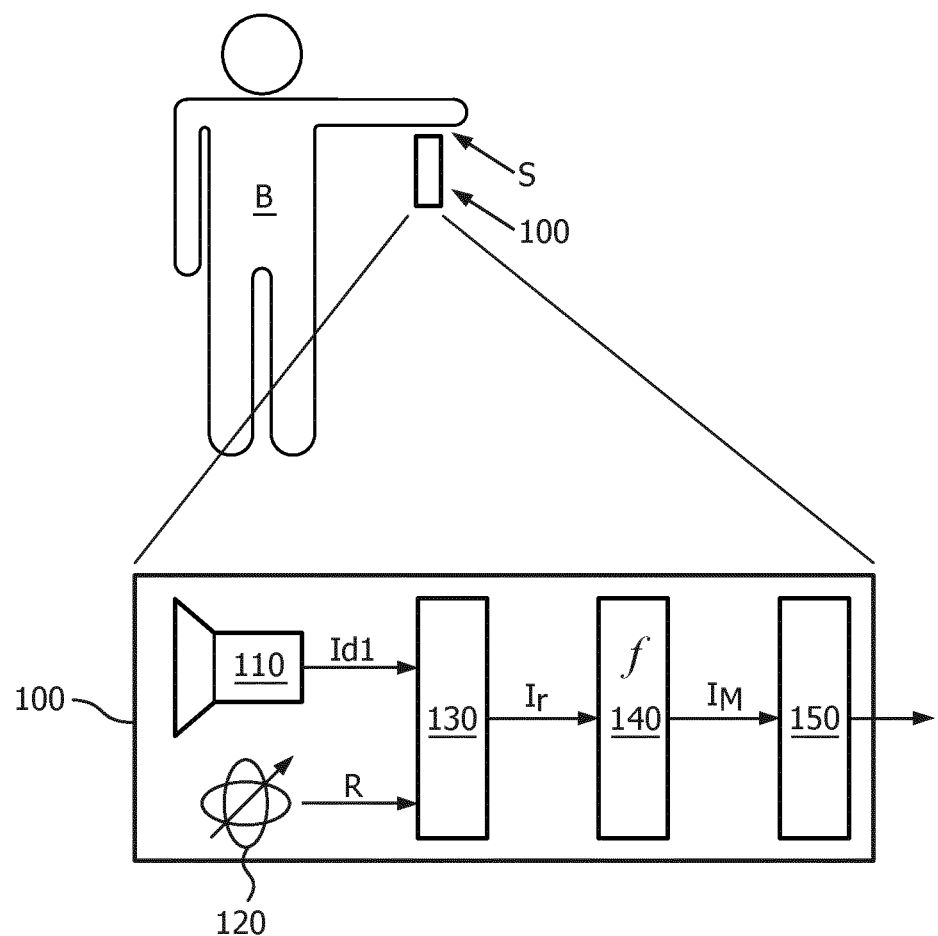
FIG. 10 illustrates an embodiment of a skin analysis system according to the third aspect of the invention.

FIG. 10 schematically shows a skin analysis system 100, here provided in a single portable housing, for analysis of skin S of a mammal body B.

The skin analysis system 100 comprises a skin imaging camera 110 to capture a plurality of images of the skin S and to provide respective image data Id1 representative of the plurality of images. The system further comprises an orientation determining device 120 to provide respective orientation information data R representative of an orientation of the skin imaging camera 110. An image mapping unit 130 maps the respective image data in accordance with the orientation with which the image data was obtained as indicated by the orientation information data and provides respective mapped image data $I_R$ representing the result of this mapping. The system further comprises an image merging unit 140 to prepare a single merged image from the respective mapped image data, and to provide merged image data $I_M$ representing the single merged image.

It is noted that components of the skin analysis system 100 are not necessarily integrated in one housing. In embodiments, various components may be remotely arranged with respect to each other and exchange data with each other via wired or wireless communication means.

As another alternative, a skin analysis system 100 may be integrated with a system 1 in a common housing.

In the embodiment shown in FIG. 10, the orientation determining device 120 is an inertial sensor, in particular a gyroscope. Alternatively, the orientation determining device 120 may be an external camera that registers the orientation of the skin imaging camera 110, or it may compute an orientation for which the captured image data Id1 best matches a portion of the merged image data $I_M$, for example in a manner as described for the module 42 in FIG. 3.

In the embodiment shown in FIG. 10, the system has a data exchange facility 150 facilitating a transfer of the merged image data $I_M$ to a skin analysis system 1.

The merged image data $I_M$ may comprise raw image data, such as RGB data, HUV data, or gray value data, feature descriptor data, that specify the presence of specific features on the skin as a function of position, and/or surface normal data indicative of a surface normal of the skin as a function of position. Surface normal data may be obtained from the orientation determining device 120.

Figure 11:
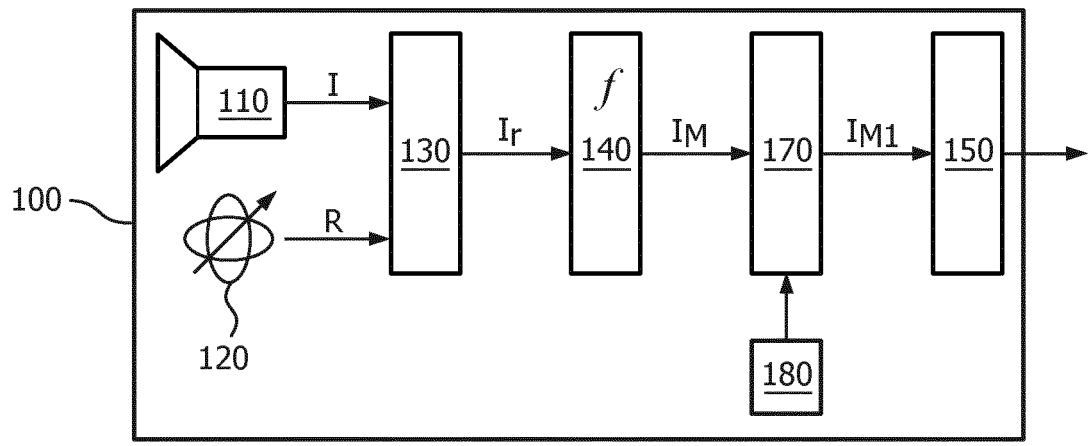
FIG. 11 illustrates an embodiment of a skin analysis system according to the third aspect of the invention.
Figure 11A:
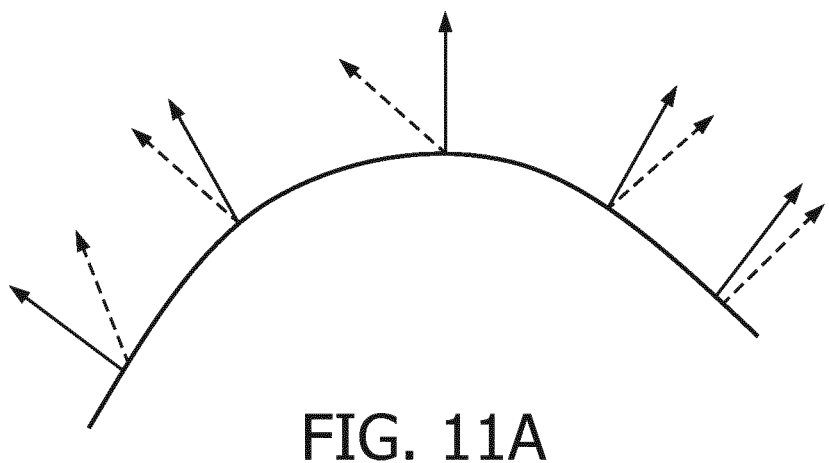
FIGS. 11A, 11B illustrate an operation of the embodiment of FIG. 11.
Figure 11B:
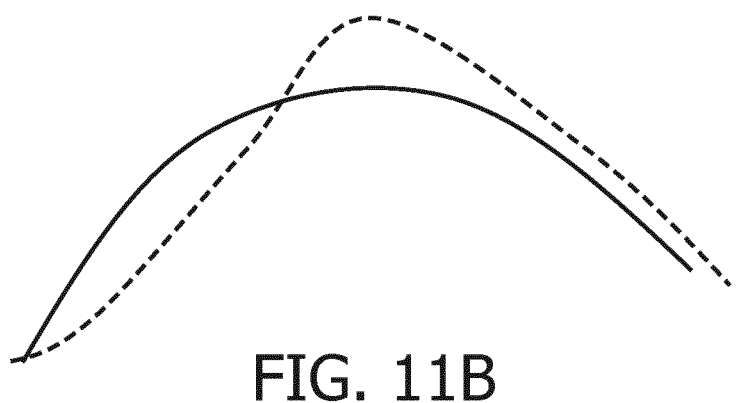

An embodiment of the skin analysis system 100, wherein surface normal data is included in the merged image data $I_M$, is illustrated in FIG. 11. In addition to the components described with reference to FIG. 10, this embodiment also includes a correction facility comprising a correction module 170 to compare a 3D profile as obtained from the merged image data $I_M$ with a generic 3D body profile stored in a storage unit 180 and to provide merged image data $I_M$ with a corrected 3D profile. The operation of the correction facility 170, 180 is illustrated in FIGS. 11A, 11B. In FIG. 11A, the solid curve illustrates an actual profile of the skin S of a body B. The solid arrows illustrate the surface normal as determined by orientation determining device 120. As the operator may not always keep the skin analysis system 100 perpendicularly to the skin, the determined surface normal (indicated by dashed arrows in FIG. 11A) may deviate from the actual surface normal. As a result, the 3D profile (See dashed curve in FIG. 11B) of the skin that would be obtained directly on the basis of the measurements of the orientation determining device 120 would clearly deviate from the actual profile. The correction facility 170, 180 provides secondary merged image data $I_{M1}$, wherein the accuracy of the 3D profile is improved, as illustrated by the solid curve in FIG. 11B. To that end, the correction module 170 may for example apply a curve fitting method using the input data for the surface normal obtained by device 120 and general specifications, specified for the curve, provided in storage unit 180.

Figure 12:
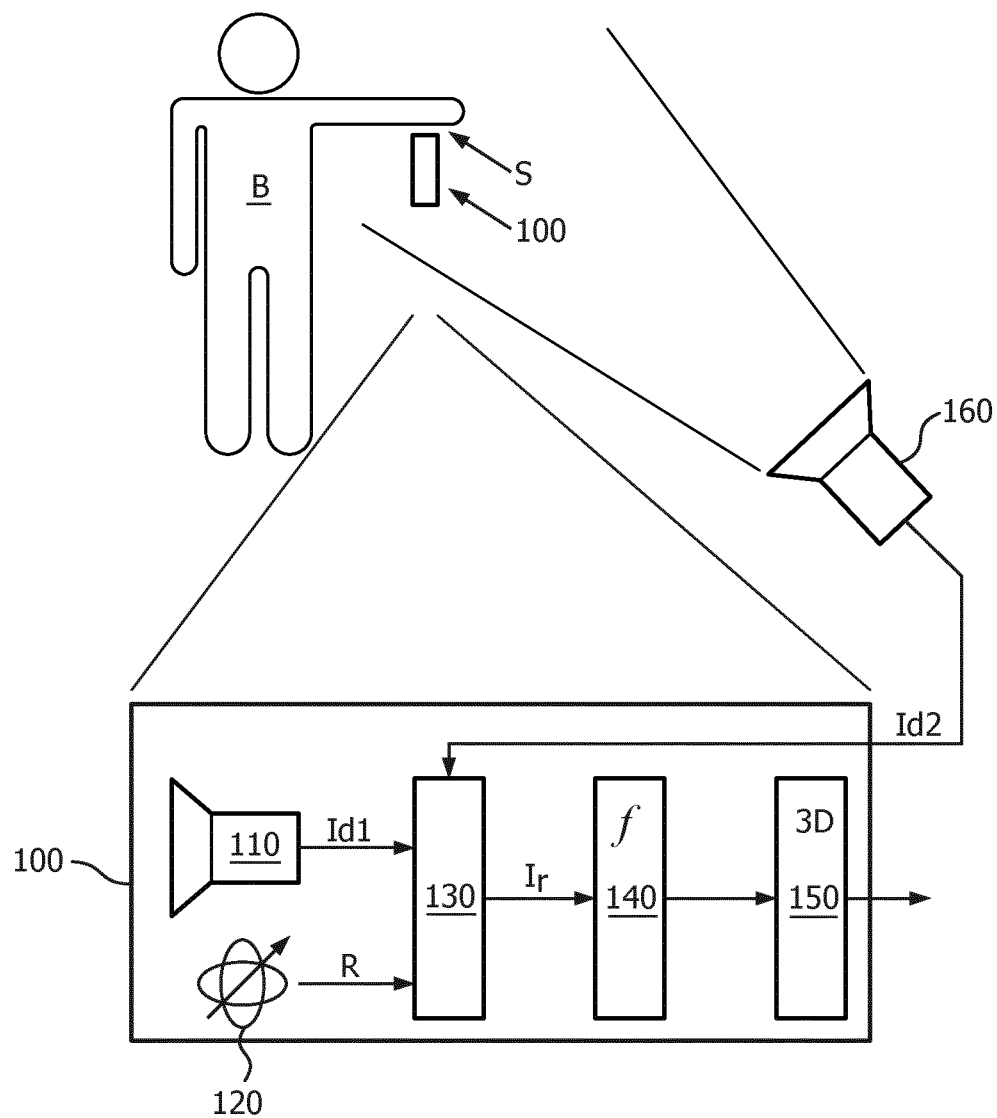
FIG. 12 illustrates an embodiment of a skin analysis system according to the third aspect of the invention, FIG. 13 serves to illustrate a spatial configuration of a skin analysis system as shown in FIG. 14.

FIG. 12 illustrates an alternative embodiment of the skin analysis system 100, which in addition to the components as specified for the system of FIG. 10 also includes a further camera 160 having a field of view including at least a part of the skin imaging camera 110 and at least a part of the mammal body B. The image mapping unit 130 also uses the image data Id2 to determine the orientation of the skin imaging camera 110 with respect to the skin S.

Figure 14:
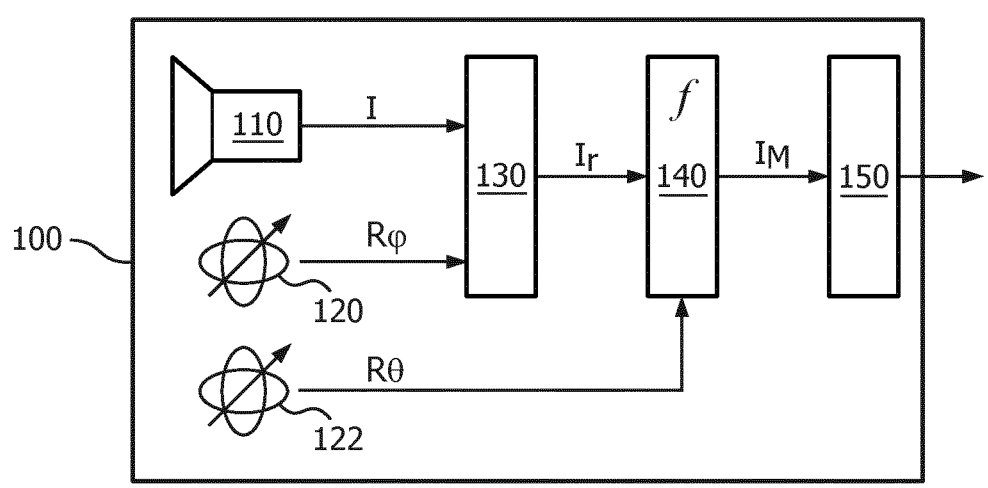
FIG. 14 illustrates an embodiment of a skin analysis system according to the third aspect of the invention.

FIGS. 13 and 14 illustrate a further embodiment, wherein the skin analysis system 100 includes a first gyroscope 120 and a second gyroscope 122 as an orientation determining device. As illustrated in FIG. 13, the skin imaging camera 110 has an azimuthal angle $\varphi$, and a polar angle $\theta$, with respect to the plane x,y as locally defined by the skin surface. The first gyroscope 120 and the second gyroscope 122 detect these angles and issue an indication $R\varphi$, $R\theta$, respectively, that is indicative of the value of these angles. The azimuthal angle indicates the in-plane rotation of the camera and $R\varphi$ is used to more easily match the captured image to the total image for merging. Information about the polar angle and possibly the azimuthal angle is added to the merged image as a feature, i.e. including $R\varphi$, $R\theta$ as a function of x,y in the final merged image.

It is noted that data processing facilities used in the skin treatment system 1 and/or the skin analysis system 100 may be implemented in various ways. For example, these facilities may be provided as a suitably programmed general purpose processor, as dedicated hardware, i.e. specifically designed for performing the specified data processing tasks, or as partly programmable processors having some dedicated hardware and being programmable in a restricted application range. Also combinations of such elements may be used.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite article "a" or "an" is employed to describe elements and components of the invention. This is done merely for convenience and to give a general sense of the invention. This description should be read to include one or at least one, and the singular also includes the plural unless it is obvious that it is meant otherwise.

The invention claimed is:

1. A skin treatment system comprising:
   a treatment device configured to treat a treatment region of a mammal body by physically acting upon the mammal body in said treatment region;
   a camera configured to capture at least one image of skin of the mammal body having an imaging region and provide captured image data representative of said at least one captured image, said imaging region having a predefined spatial relationship with said treatment region;
   a storage facility configured to store reference image data indicative of a reference image of the skin of the mammal body, wherein said reference image includes body features represented in said reference image data, and wherein said body features may change over time and are independent of said treatment device acting upon the mammal body;
   an orientation estimation facility is configured to determine which part of said reference image corresponds to said at least one captured image, using said captured image data, said reference image data and said body features, and derive from a predetermined orientation of said corresponding part with respect to the reference image an orientation indication indicative of an orientation of the treatment device with respect to the mammal body; and an update unit configured to update said reference image data in response to at least one of a model specifying an expected development over time of said body features represented in said reference image data or a change in said body features between said captured image data and said reference image data.

2. The skin treatment system according to claim 1, further comprising an analysis facility configured to use said orientation indication to provide a treatment indication indicative of an extent to which a treatment was applied to the mammal body as a function of a position on the mammal body.

3. The skin treatment system according to claim 2, further comprising a display configured to provide a visual representation of said treatment indication.

4. The skin treatment system according to claim 2, further comprising a controller configured to control the treatment device in accordance with said treatment indication.

5. The skin treatment system according to claim 1, further comprising an arrangement of a body treatment module and a processing module that are mutually functionally coupled and, at least within an operational range, independently movable with respect to each other, wherein the body treatment module at least comprises the treatment device and the camera integrated therewith, and wherein the processing module at least comprises the storage facility and the orientation estimation facility.

6. The skin treatment system according to claim 1, wherein said treatment device is a photon radiation device which is configured to irradiate the skin with photon radiation to physically affect the mammal body in the treatment region.

7. A skin treatment system comprising:
a treatment device configured to treat a treatment region of a mammal body by physically acting upon the mammal body in said treatment region;
a camera configured to capture at least one image of skin of the mammal body having an imaging region and provide captured image data representative of said at least one captured image, said imaging region having a predefined spatial relationship with said treatment region;
a storage facility configured to store reference image data indicative of a reference image of the skin of the mammal body;
an orientation estimation facility is configured to determine which part of said reference image corresponds to said at least one captured image, using said captured image data and said reference image data, and derive from a predetermined orientation of said corresponding part with respect to the reference image an orientation indication indicative of an orientation of the treatment device with respect to the mammal body; and
an analysis facility configured to use said orientation indication to provide a treatment indication indicative of an extent to which a treatment was applied to the mammal body as a function of a position on the mammal body,
wherein said treatment device is a hair clipper which is configured to clip hairs on the skin in the treatment region to physically affect the mammal body in the treatment region, wherein said treatment indication is a binary representation of where hair has been previously clipped or not clipped.

8. The skin treatment system according to claim 1, wherein said update unit is configured to update said reference image data when said body features between said captured image data and said reference image data change more than a predetermined threshold.

9. A method of determining an orientation of a skin treatment device with respect to a mammal body, said skin treatment device defining a treatment region on said mammal body upon which the skin treatment device physically acts during operation, the method comprising acts of:
capturing at least one image having an imaging region of skin of the mammal body and providing image data representative of said at least one captured image, said imaging region having a predefined spatial relationship with said treatment region;
storing reference image data indicative of a reference image of the skin of the mammal body, wherein said reference image includes body features represented in said reference image data, and wherein said body features may change over time and are independent of said treatment device acting upon the mammal body;
determining which part of said reference image corresponds to said at least one captured image, using said image data, said reference image data and said body features;
deriving from a predetermined orientation of said corresponding part with respect to the reference image an orientation indication indicative of an orientation of said treatment region with respect to said skin; and
updating said reference image data in response to at least one of a model specifying an expected development over time of said body features represented in said reference image data or a change in said body features between said captured image data and said reference image data.

10. A skin analysis system for analysis of skin of a mammal body, comprising:
a skin imaging camera configured to capture a plurality of images of said skin, and provide respective image data representative of said plurality of images;
a storage facility configured to store reference image data indicative of a reference image of said skin, wherein said reference image includes body features represented in said reference image data, and wherein said body features may change over time independent of a treatment device acting upon the mammal body;
an orientation determining device configured to provide respective orientation information data representative of an orientation of the skin imaging camera based on said captured plurality of images, said reference image data and said body features;
an image mapping unit configured to map said respective image data in dependence on the orientation of the skin imaging camera at which the image data was respectively obtained as indicated by said respective orientation information data, and provide respective mapped image data representing the result of this mapping;
an image merging unit configured to prepare a single merged image from the respective mapped image data, and provide merged image data representing the single merged image; and
an update unit configured to update said reference image data in response to at least one of a model specifying an expected development over time of said body features represented in said reference image data or a change in said body features between said captured plurality of images and said reference image data.

11. The skin analysis system according to claim 10, wherein said orientation determining device comprises a gyroscope.

12. The skin analysis system according to claim 10, wherein said orientation determining device comprises a further camera configured to have a field of view including at least a part of the skin imaging camera and at least a part of the mammal body, configured to capture at least one image from said field of view and configured to provide image data indicative of said captured image to said image mapping unit, and wherein said image mapping unit is configured to use said image data to determine the orientation of the skin imaging camera with respect to the skin.

13. The skin analysis system according to claim 10, further comprising a correction facility configured to compare a 3D profile obtained from the merged image data with a generic 3D body profile and to provide a corrected 3D profile based on said comparison.

14. The skin analysis system according to claim 10, further comprising a data exchange facility configured to enable a transfer of said merged image data to an external device.

15. The skin analysis system according to claim 10, wherein said image merging unit is configured to prepare the reference image from the respective mapped image data mapped by the image mapping unit.

16. A method of analyzing skin of a mammal body, the method comprising acts of:
    capturing a plurality of images of said skin by means of a skin imaging camera and providing respective image data representative of said plurality of images;
    storing reference image data indicative of a reference image of said skin, wherein said reference image includes body features represented in said reference image data, and wherein said body features may change over time independent of a treatment device acting upon the mammal body;
    providing respective orientation information data representative of an orientation of the skin imaging camera at which said plurality of images are respectively captured, wherein said respective orientation information data is based on said captured plurality of images, said reference image data and said body features;
    mapping said plurality of images in dependence on the orientation of the skin imaging camera at which the respective image data was obtained as indicated by said orientation information data;
    providing respective mapped image data representing the result of the mapping;
    preparing a single merged image from the respective mapped image data;
    providing merged image data representing the single merged image;
    comparing the single merged image data to reference image data; and
    updating said reference image data in response to at least one of a model specifying an expected development over time of said body features represented in said reference image data or a change in said body features between the single merged image data and said reference image data.

17. The method of analyzing skin according to claim 16, further comprising an act of analyzing the skin, wherein the act of preparing the single merged image comprises an act of preparing the reference image from the respective mapped image data.

18. The skin treatment system according to claim 1, further comprising an analysis facility configured to use said orientation indication to determine a treatment indication indicative of an extent to which a treatment was applied to the mammal body as a function of a position on the mammal body;
    wherein said treatment device is configured to physically affect the mammal body in said treatment region, and wherein said treatment indication is a binary representation of where treatment has been applied or has not been applied.

19. The method according to claim 9, further comprising an act of determining a treatment indication indicative of an extent to which a treatment was applied to the mammal body as a function of a position on the mammal body determined using said orientation indication;
    wherein said treatment device during operation physically affects the mammal body in said treatment region, and wherein said treatment indication is a binary representation of where treatment has been applied or has not been applied.

20. The skin analysis system according to claim 10, further comprising an analysis facility configured to use said respective orientation information data to determine a treatment indication indicative of an extent to which a treatment was applied to the mammal body as a function of a position on the mammal body;
    wherein said treatment device is configured to physically affect the mammal body in a treatment region, and wherein said treatment indication is a binary representation of where treatment has been applied or has not been applied.

* * * * *